(12) United States Patent
McMurtry et al.

(10) Patent No.: US 7,300,415 B2
(45) Date of Patent: Nov. 27, 2007

(54) BALLOON CATHETER HAVING AN EXTERNAL GUIDEWIRE

(75) Inventors: Christopher McMurtry, Murrieta, CA (US); Jeong S. Lee, Diamond Bar, CA (US); Kenneth L. Wantink, Temecula, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 608 days.

(21) Appl. No.: 10/326,359

(22) Filed: Dec. 20, 2002

(65) Prior Publication Data

US 2004/0122465 A1 Jun. 24, 2004

(51) Int. Cl.
*A61M 29/00* (2006.01)
(52) U.S. Cl. ........................................ 604/96; 606/194
(58) Field of Classification Search ........ 606/191–199; 604/95.03, 96.01, 101.01, 101.02, 101.03, 604/102.01, 95.3, 96.1, 101.1, 101.2, 101.3, 604/102.1
See application file for complete search history.

(56) References Cited

U.S. PATENT DOCUMENTS

| | | | |
|---|---|---|---|
| 4,881,547 A | 11/1989 | Danforth | |
| 5,090,958 A | 2/1992 | Sahota | |
| 5,267,958 A | 12/1993 | Buchbinder et al. | |
| 5,324,263 A * | 6/1994 | Kraus et al. | 604/96.01 |
| 5,383,853 A | 1/1995 | Jung | |
| 5,413,557 A | 5/1995 | Solar | |
| 5,458,639 A | 10/1995 | Tsukashima et al. | |
| 5,533,968 A * | 7/1996 | Muni et al. | 604/103.11 |
| 5,549,556 A | 8/1996 | Ndondo-Lay et al. | |
| 5,575,771 A | 11/1996 | Walinsky | |
| 5,578,009 A * | 11/1996 | Kraus et al. | 604/95.04 |
| 5,616,149 A | 4/1997 | Barath | |
| 5,718,683 A | 2/1998 | Ressemann | |
| 5,830,227 A | 11/1998 | Fischell et al. | |
| RE36,104 E | 2/1999 | Solar | |
| 5,882,334 A * | 3/1999 | Sepetka et al. | 604/164.08 |
| 6,071,285 A | 6/2000 | Lashinski et al. | |
| 6,322,577 B1 * | 11/2001 | McInnes | 606/194 |
| 6,394,995 B1 | 5/2002 | Solar et al. | |
| 6,447,501 B1 | 9/2002 | Solar et al. | |
| 6,544,219 B2 | 4/2003 | Happ | |
| 6,740,104 B1 | 5/2004 | Solar et al. | |
| 6,780,199 B2 | 8/2004 | Solar | |
| 6,863,678 B2 * | 3/2005 | Lee et al. | 606/192 |

* cited by examiner

*Primary Examiner*—Michael J. Hayes
*Assistant Examiner*—Victor Nguyen
(74) *Attorney, Agent, or Firm*—Fulwider Patton LLP

(57) ABSTRACT

A catheter having an elongated shaft with an inflation lumen and a guidewire lumen, a balloon on a distal shaft section, and a proximal intermediate port proximal to the balloon and a distal intermediate port distal to the balloon, the intermediate ports being in communication with the guidewire lumen and being configured to slidably receive a guidewire therethrough so that the guidewire extends into or out of a proximal section of the guidewire lumen through the proximal intermediate port, extends along an outer surface of the balloon, and extends into or out of a distal section of the guidewire lumen through the distal intermediate port. The balloon is inflated in a patient's blood vessel to perform a medical procedure, with the section of the guidewire extending along an outer surface of the balloon providing improved balloon retention at the desired location in the blood vessel during inflation of the balloon.

17 Claims, 4 Drawing Sheets

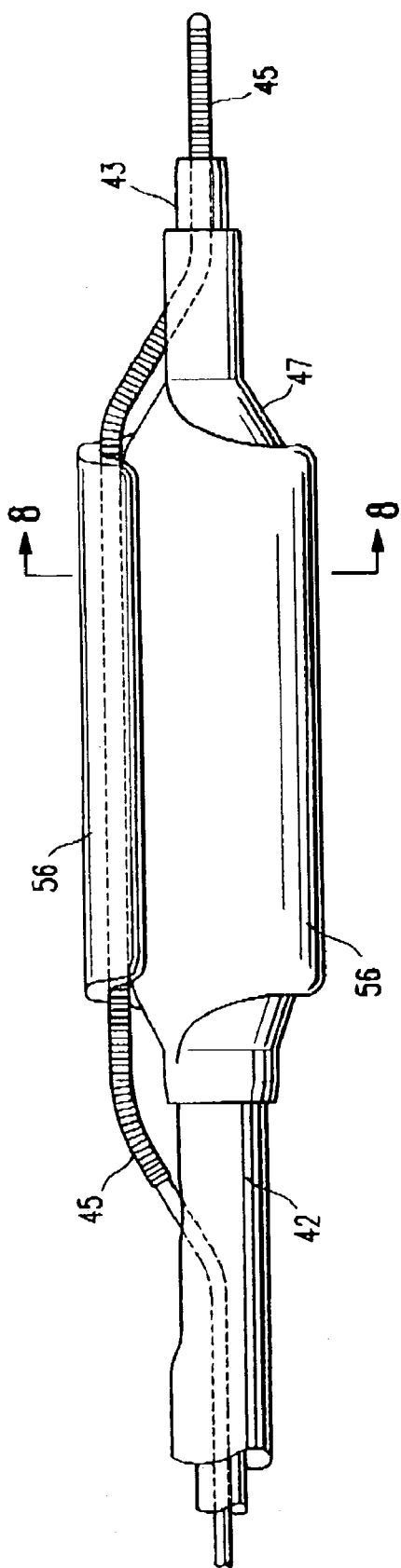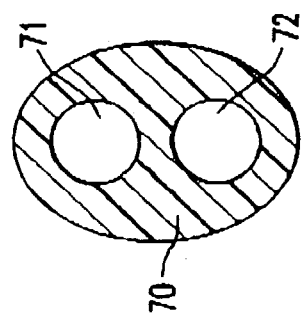

BALLOON CATHETER HAVING AN EXTERNAL GUIDEWIRE

BACKGROUND OF THE INVENTION

This invention generally relates to catheters, and particularly intravascular catheters for use in percutaneous transluminal coronary angioplasty (PTCA) or for the delivery of stents.

In percutaneous transluminal coronary angioplasty (PTCA) procedures a guiding catheter is advanced in the patient's vasculature until the distal tip of the guiding catheter is seated in the ostium of a desired coronary artery. A guidewire is first advanced out of the distal end of the guiding catheter into the patient's coronary artery until the distal end of the guidewire crosses a lesion to be dilated. A dilatation catheter, having an inflatable balloon on the distal portion thereof, is advanced into the patient's coronary anatomy over the previously introduced guidewire until the balloon of the dilatation catheter is properly positioned across the lesion. Once properly positioned, the dilatation balloon is inflated with inflation fluid one or more times to a predetermined size at relatively high pressures so that the stenosis is compressed against the arterial wall and the wall expanded to open up the vascular passageway. Generally, the inflated diameter of the balloon is approximately the same diameter as the native diameter of the body lumen being dilated so as to complete the dilatation but not over expand the artery wall. After the balloon is finally deflated, blood resumes through the dilated artery and the dilatation catheter and the guidewire can be removed therefrom.

In such angioplasty procedures, there may be restenosis of the artery, i.e. reformation of the arterial blockage, which necessitates either another angioplasty procedure, or some other method of repairing or strengthening the dilated area. To reduce the restenosis rate of angioplasty alone and to strengthen the dilated area, physicians now normally implant an intravascular prosthesis, generally called a stent, inside the artery at the site of the lesion. Stents may also be used to repair vessels having an intimal flap or dissection or to generally strengthen a weakened section of a vessel or to maintain its patency. Stents are usually delivered to a desired location within a coronary artery in a contracted condition on a balloon of a catheter which is similar in many respects to a balloon angioplasty catheter, and expanded within the patient's artery to a larger diameter by expansion of the balloon. The balloon is deflated to remove the catheter and the stent left in place within the artery at the site of the dilated lesion. See for example, U.S. Pat. No. 5,507,768 (Lau, et al.)and U.S. Pat. No. 5,458,615 (Klemm, et al.), which are incorporated herein by reference.

An essential step in effectively performing a PTCA procedure is properly positioning the balloon catheter at a desired location within the coronary artery. To properly position the balloon at the stenosed region, the catheter must have good pushability (i.e., ability to transmit force along the length of the catheter) and flexibility to be readily advanceable within the tortuous anatomy of the patient's vasculature. Conventional balloon catheters for intravascular procedures, such as angioplasty and stent delivery, frequently have relatively a stiff proximal shaft section to facilitate advancement of the catheter within the patient's body lumen and a relatively flexible distal shaft section to facilitate passage through tortuous anatomy such as distal coronary and neurological arteries without damage to the luminal wall. To facilitate advancement of the catheter within the tortuous vasculature, conventional balloon catheters for angioplasty and stent delivery frequently have a lubricious coating on at least a portion of an outer surface of the catheter. However, one difficulty has been the tendency of the balloon having a lubricious coating thereon to slip out of position during inflation of the balloon. Accordingly, it would be a significant advance to provide a catheter balloon having improved balloon retention, and without inhibiting movement of the catheter within the vasculature.

SUMMARY OF THE INVENTION

The invention is directed to a catheter having an elongated shaft with an inflation lumen and a guidewire lumen, a balloon on a distal shaft section, a guidewire proximal port, a guidewire distal port, a proximal intermediate port proximal to the balloon, and a distal intermediate port distal to the balloon. The intermediate ports are intermediate to (i.e., between) the guidewire proximal and distal ports and in communication with the guidewire lumen, and are configured to slidably receive a guidewire therethrough so that the guidewire extends into or out of a proximal section of the guidewire lumen through the proximal intermediate port, extends along an outer surface of the balloon, and extends into or out of a distal section of the guidewire lumen through the distal intermediate port. The balloon is inflated in a patient's blood vessel to perform a medical procedure, with the section of the guidewire extending along an outer surface of the balloon providing improved balloon retention at the desired location in the blood vessel during inflation of the balloon.

The balloon catheter of the invention may comprise a variety of suitable balloon catheters, including coronary and peripheral dilatation catheters, stent delivery catheters, drug delivery catheters, and the like. A balloon catheter of the invention generally comprises an elongated shaft with an inflation lumen and a guidewire lumen, and an inflatable balloon on the distal shaft section having an interior in fluid communication with the inflation lumen. The guidewire lumen has a guidewire proximal port and the proximal intermediate port located proximal to the balloon, and a guidewire distal port and the distal intermediate port located distal to the balloon. The proximal intermediate port is located distal to the guidewire proximal port, and the distal intermediate port is located proximal to the guidewire distal port. The guidewire lumen extends at least between the guidewire proximal port and the proximal intermediate port, and at least between the guidewire distal port and the distal intermediate port. Thus, the guidewire extends along an outer surface of the balloon but proximal and distal to the balloon it is within sections of the guidewire lumen located between the intermediate ports and the guidewire ports. As a result, the tendency of a guidewire external to the catheter shaft to become wrapped or tangled with the catheter shaft during torquing of the catheter within the patient's body lumen is prevented or inhibited.

In one embodiment, the catheter is a rapid exchange type catheter having the guidewire proximal port located distal to the proximal end of the shaft, and preferably in the distal shaft section spaced a relatively short distance proximally from the guidewire distal port and a relatively long distance distally from the proximal end of the catheter shaft, with a relatively short guidewire receiving lumen extending in the distal shaft section. In an alternative embodiment, the catheter is an over-the-wire type catheter having the guidewire proximal port at the proximal end of the catheter.

In one embodiment, the tubular shaft has a portion which extends in the balloon interior. The shaft portion in the balloon interior preferably provides support for the balloon, to preferably prevent or inhibit the balloon from bowing during inflation of the balloon or from or axially bunching during advancement in the patient's body lumen. The tubular shaft portion extending through the balloon interior defines a lumen which typically is an extension of the guidewire lumen. However, in a presently preferred embodiment, the lumen of the shaft portion extending through the balloon interior is not in fluid communication with the portion of the guidewire lumen located proximal to the proximal intermediate port and/or with the portion of the guidewire lumen located distal to the distal intermediate port. Specifically, in one embodiment, a support member is in the shaft lumen extending along at least part of the length between the proximal and distal intermediate ports, so that the support member occludes the lumen. In a presently preferred embodiment, the support member has a length which extends from the proximal intermediate port to the distal intermediate port, so that the support member is in the lumen of the shaft portion extending through the balloon interior to preferably provide additional support at the balloon. The support member is typically a metallic and/or polymeric mandrel (e.g., rod or plug), and in one embodiment the ends of the support member are configured to provide a surface which guides the guidewire out of the guidewire lumen and along the outer surface of the balloon. The shaft portion is typically shrunk down onto the support member, so that the support member fully occludes the lumen therein. In alternative embodiments, the support member only partially occludes the lumen, with a space remaining between the support member and the inner surface of the shaft, although the space is typically sufficiently small that the support member nonetheless prevents the guidewire from extending in the part of the shaft lumen having the support member therein. In an alternative embodiment, the tubular shaft does not extend through the balloon interior from the proximal to the distal end of the balloon. However, in the embodiment in which the tubular shaft does not extend through the balloon interior, a support member such as a mandrel or rod is typically provided which extends through the balloon interior.

In one embodiment, the elongated shaft comprises an outer tubular member defining the inflation lumen, and an inner tubular member defining the guidewire lumen and extending within the outer tubular member lumen and distally therebeyond through the balloon interior. However, a variety of suitable shaft configurations may be used as are conventionally known, including a dual lumen type shaft having a first lumen forming the guidewire lumen and a second lumen forming the inflation lumen in side-by-side relation thereto. In the dual lumen type shaft design, the shaft portion extending through the balloon interior may be formed by a tubular extension extending distally from the distal end of the dual-lumen polymeric tube, or alternatively, a support member such as a mandrel or rod may extend alone from the distal end of the dual-lumen polymeric tube and without a tubular shaft section therearound.

A method of performing a medical procedure using a balloon catheter embodying features of the invention generally comprises positioning the balloon so that the balloon working length extends along the stenosed section of the blood vessel, and inflating the balloon. In a presently preferred embodiment, the medical procedure is dilating a stenosis, so that the balloon dilates the stenosed section of the blood vessel, with the section of the guidewire along the outer surface of the balloon contacting the stenosed section of the blood vessel wall during inflation of the balloon to preferably frictionally engage the blood vessel wall. The guidewire thus facilitates dilating the stenosis, by enhancing the ability of the inflated balloon to remain in position in contact with the stenosed section of the blood vessel wall, with an insubstantial amount of longitudinal slippage proximally or distally from the desired position in the blood vessel. In one embodiment, the guidewire has a rounded outer surface which prevents or inhibits damage to the blood vessel wall as the balloon presses the guidewire against the blood vessel wall.

In one embodiment, the section of the guidewire extending along the outer surface of the balloon is on an exposed section of the outer surface of the noninflated balloon. The deflated balloon typically forms wings which are wrapped around the outside of the balloon, or otherwise forms a folded configuration, providing a low profile configuration for introduction and advancement of the catheter within the patient's body lumen prior to inflation of the balloon in the body lumen. In the folded configuration, the outer surface of the balloon has an exposed first section and an unexposed second section, and the inflated configuration exposes both the first and second sections of the balloon outer surface. In one embodiment, the section of the guidewire extending along the outer surface of the balloon is located outside the unexposed channel formed by the folded wings in the folded configuration, and is thus on an exposed section of the outer surface of the balloon. In an alternative embodiment, the section of the guidewire extending along the outer surface of the balloon extends at least in part within the unexposed channel formed by the fold wings (i.e., along an unexposed section of the outer surface of the balloon in the folded configuration). With the guidewire passing through the channel formed under the wing between the wing and the underlying section of the outer surface of the balloon in the folded configuration, the guidewire tends to be guided or directed into the proximal intermediate port during insertion of the catheter over the guidewire.

The balloon catheter has improved balloon retention during inflation of the balloon in the patient's body lumen, due to the catheter configuration having a section of the guidewire extending along the outer surface of the balloon. The portion of the guidewire extending along the outer surface of the inflated balloon preferably frictionally engages the wall of the body lumen, preferably without damaging the body lumen wall. Moreover, the shaft configuration provides improved support at the balloon for enhanced catheter performance. These and other advantages of the invention will become more apparent from the following detailed description of the invention and the accompanying exemplary drawings.

BRIEF DESCRIPTION OF THE DRAWINGS

FIG. 7 is an enlarged elevational view of a distal section of an alternative embodiment, having the guidewire underneath a wing of a folded balloon.

FIG. 8 is a transverse cross sectional view of the catheter of FIG. 7 taken along line 8-8.

FIG. 9 is a transverse cross sectional view of an alternative embodiment having a dual lumen extruded shaft.

DETAILED DESCRIPTION OF THE INVENTION

Figure 1:
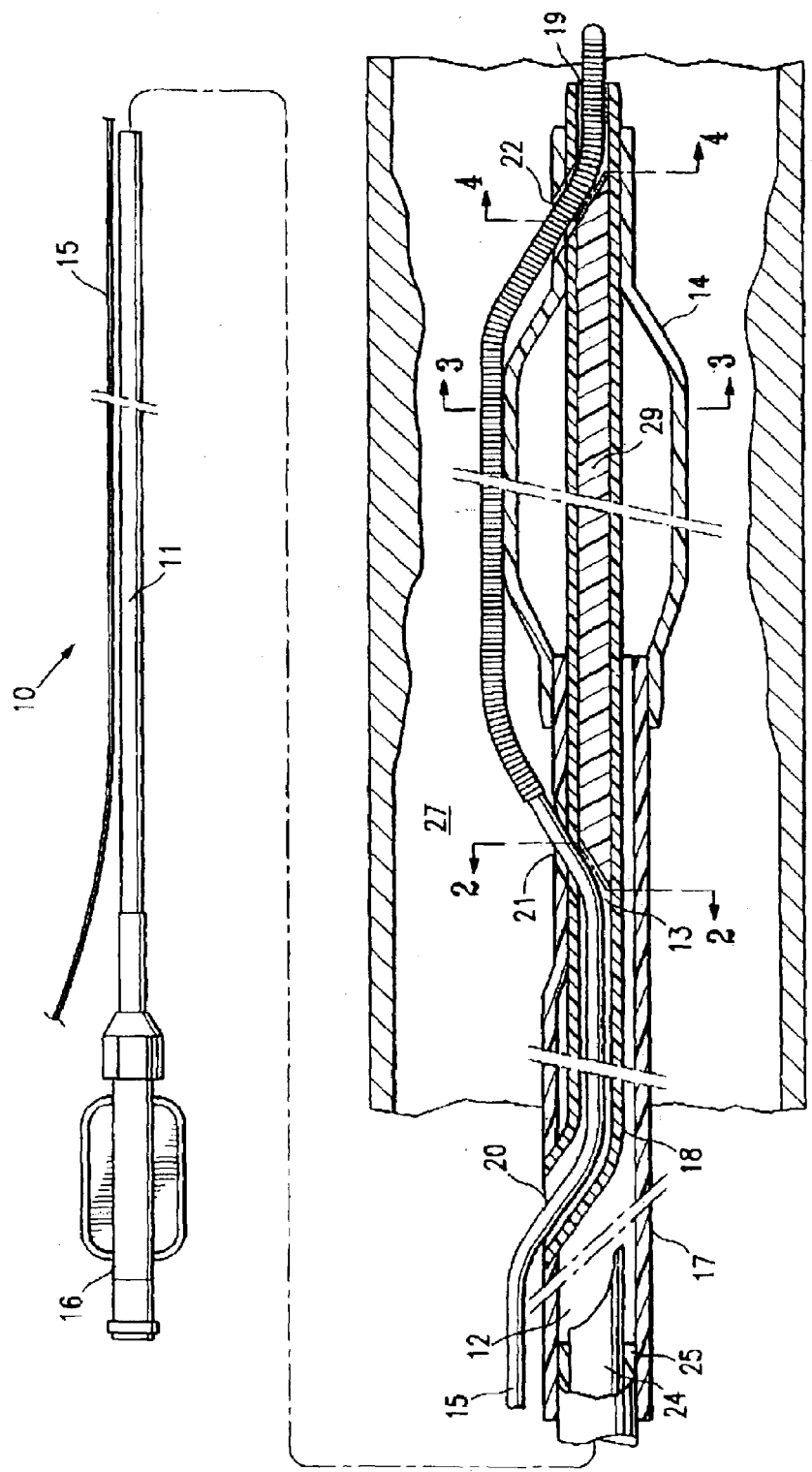
FIG. 1 is an elevational view, partially in section, of a rapid exchange type balloon catheter which embodies features of the invention.

FIG. 1 illustrates a rapid exchange type balloon catheter 10, generally comprising a shaft 11 with an inflation lumen 12, a guidewire lumen 13 in a distal shaft section configured to slidingly receive a guidewire 15, and a balloon 14 on the distal shaft section. An adapter 16 at the proximal end of catheter shaft 11 is configured to direct inflation fluid into inflation lumen 12. FIG. 1 illustrates the balloon 14 prior to complete inflation within the patient's body lumen 27. In use, the distal end of catheter 10 is advanced to a desired region of the patient's body lumen 27 in a conventional manner either over a previously positioned guidewire, or with guidewire 15 already in the catheter 10. The balloon 14 is inflated to perform a procedure, which in a preferred embodiment comprises dilating a stenosed region of the body lumen, or a previously stented body lumen that is restenosed (commonly referred to as in-stent-restenosis), and the balloon deflated for repositioning or removing the catheter 10 from the body lumen. However, the balloon catheter may be suitable for a variety of intraluminal procedures, such as expanding a stent (not shown) mounted on the balloon.

In the embodiment of FIG. 1, a distal section of the shaft 11 comprises an outer tubular member 17 defining the inflation lumen 12, and an inner tubular member 18 defining the guidewire lumen 13 extending from a guidewire distal port 19 in the distal end of the catheter shaft to a guidewire proximal port 20 spaced distally from the proximal end of the catheter shaft. A proximal shaft section comprises a tubular member, which in the embodiment of FIG. 1 is a metallic tubular member 24 having a polymeric jacket 25 on an outer surface thereof, defining a proximal section of the inflation lumen 12. Inflatable balloon 14 has an elongated cylindrical expandable working section, a proximal skirt section sealingly secured to the distal end of outer tubular member 17 and a distal skirt section sealingly secured to the distal end of inner tubular member 18, so that its interior is in fluid communication with inflation lumen 12. The tubular shaft 11 thus has a portion extending through the interior of balloon 14. Although the shaft portion extending through the interior of balloon 14 in the embodiment of FIG. 1 is an integral extension of the inner tubular member 18, in alternative embodiments (not shown), a shaft portion extending through the interior of the balloon 14 is formed by a separate tubular member secured to the shaft 11 at a location adjacent to the proximal end of the balloon 14.

Figure 4:
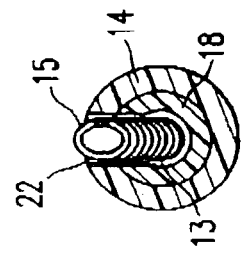
FIGS. 2-4 are transverse cross sectional views of the catheter shown in FIG. 1, taken along lines 2-2, 3-3, and 4-4, respectively.
Figure 3:
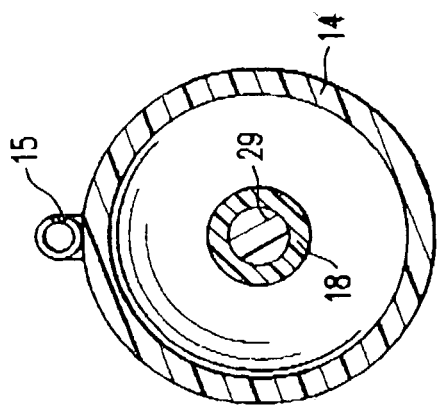
Figure 2:
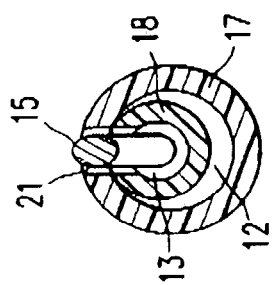

A proximal intermediate port 21 in communication with the guidewire lumen 13 is located proximal to the balloon 14 and distal to the guidewire proximal port 20. A distal intermediate port 22 in communication with the guidewire lumen 13 is located distal to the balloon 14 and proximal to the guidewire distal port 19. The proximal and distal intermediate ports 21, 22 extend through a sidewall of the outer tubular member 17 and a sidewall of the inner tubular member 18, allowing the guidewire to enter/exit a proximal section of the guidewire lumen through the proximal intermediate port 21 and exit/enter a distal section of the guidewire lumen 13 through the distal intermediate port 22. The guidewire 15 thus extends outside the catheter and along an outer surface of the balloon 14 between the two intermediate ports 21, 22. FIGS. 2-4 illustrate transverse cross sections of FIG. 1, taken along lines 2-2, 3-3, and 4-4, respectively. Although in the illustrated embodiment the proximal intermediate port 21 extends through the sidewall a polymeric tube forming outer tubular member 17, in alternative embodiments (not shown), the outer tubular member 17 may comprises multiple tubes joined lengthwise, end-to-end, with the intermediate port 21 formed by the end opening of one of the tubes.

The distal intermediate port 22 extends through the sidewall of both the balloon distal skirt section and the underlying inner tubular member 18 in the embodiment of FIG. 1, for increased support at the distal intermediate port 22. However, in alternative embodiments (not shown), the distal intermediate port 22 may be located distal to the distal end of the balloon distal skirt section. In the embodiment of FIG. 1, the proximal intermediate port 21 is formed by joining a portion of the inner surface of the outer tubular member 17 to a portion of the outer surface of the inner tubular member 18. For example, the outer tubular member may be pressed down onto the inner tubular member and heated, to heat fuse thereto. The proximal intermediate port 21 is then formed by drilling through, or otherwise removing material from, the outer and inner tubular members 17, 18, to form the port 21. The portion of the outer surface of the inner tubular member 18 fused or otherwise joined to the outer tubular member 17 at the proximal intermediate port 21 extends only partially around the circumference thereof, so that the inflation lumen 12 extending along the proximal intermediate port 21 is defined by the space remaining between the outer and inner tubular members 17, 18 therealong. In the embodiment of FIG. 1, the joined portion extends to the distal end of the outer tubular member 17. Alternatively, the joined portion may extend a relatively short distance along the length of the outer tubular member 17, so that the inflation lumen 12 has an annular shape defined by the annular space between the outer and inner tubular members 17, 18 along at least a section of the shaft located proximally and distally of the proximal intermediate port 21.

In the embodiment of FIG. 1, the proximal and distal intermediate ports 21, 22 are oriented in the sidewalls to open outwardly in a direction pointing toward the balloon, and thus are not formed through the sidewall at a perpendicular angle relative to the longitudinal axis of the shaft. The proximal intermediate port 21 is preferably spaced a short distance proximally of the balloon 14, which facilitates guidewire placement through the port 21. In one embodiment, the proximal intermediate port 21 is spaced about 1 to about 10 cm from the proximal end of the balloon 14. The proximal intermediate port is typically closer to the proximal end of the balloon than to the rapid exchange guidewire port 20, and in one embodiment is about 20 to about 30 cm distally from the rapid exchange guidewire proximal port 20, although the absolute distance from the rapid exchange guidewire proximal port 20 may vary depending on factors such as the desired use of the balloon catheter 10. In alternative embodiments (not shown), the proximal intermediate port 21 may be closer to the balloon proximal end, and may extend through a longer balloon proximal skirt section. The distal intermediate port 22 is typically spaced a relatively short distance distally from the distal end of the inflatable interior portion of the balloon, and specifically in one embodiment is about 0.2 to about 1 cm distally thereof.

In the embodiment of FIG. 1, a support member 29 comprising a solid mandrel (e.g., rod) is located in the portion of the guidewire lumen 13 extending in the balloon interior. In the embodiment of FIG. 1, the support member has a wedge shaped proximal end surface located at (i.e., radially aligned with) the proximal intermediate port 21, and a wedge shaped distal end surface located at the distal intermediate port 22. In the embodiment of FIG. 1, the support member proximal and distal ends are wedge shaped or truncated to provide a surface facilitating guiding the guidewire 15 through intermediate ports 21, 22. In the embodiment of FIG. 1, the support member 29 extends the entire length between the proximal and distal intermediate ports 21, 22. However, in alternative embodiments (not shown), one or more support members are used having lengths less than the distance between the proximal and distal intermediate ports 21,22. For example, in one embodiment (not shown), a first support member with a wedge shaped proximal end is in guidewire lumen 13 at the proximal intermediate port 21, and a second support member with a wedge shaped distal end is in the guidewire lumen 13 at the distal intermediate port 22, without a section of the support member being in the section of the guidewire lumen located between the first and second support members. In the embodiment of FIG. 1 the support member 29 is a solid polymeric mandrel in the guidewire lumen 13. However, a variety of suitable support members providing support at the balloon to prevent or inhibit the balloon 14 from bowing during inflation or from axially bunching may be used, such as coiled or braided reinforcements (not shown) in the wall of the catheter shaft 11 extending through the balloon interior, although first and second support members comprising mandrels having a wedge shaped end would typically at least be provided at the intermediate ports 21,22 to facilitate guiding the guidewire 15 through intermediate ports 21, 22, as discussed above. In a presently preferred embodiment, the polymeric material forming the support member 29 is the same as the polymeric material forming the inner surface of the inner tubular member 18 therearound, such as for example high density polyethylene (HDPE) or a nylon. However, the support member 29 can be formed of a variety of suitable materials including metallic materials such as a NiTi alloy. The support member 29 is preferably secured in the guidewire lumen 13, as for example by heat shrinking the inner tubular member 18 down onto the support member 29. The support member thus completely or partially occludes the guidewire lumen 13 such that the passage therethrough of guidewire 15 is blocked.

Figure 5:
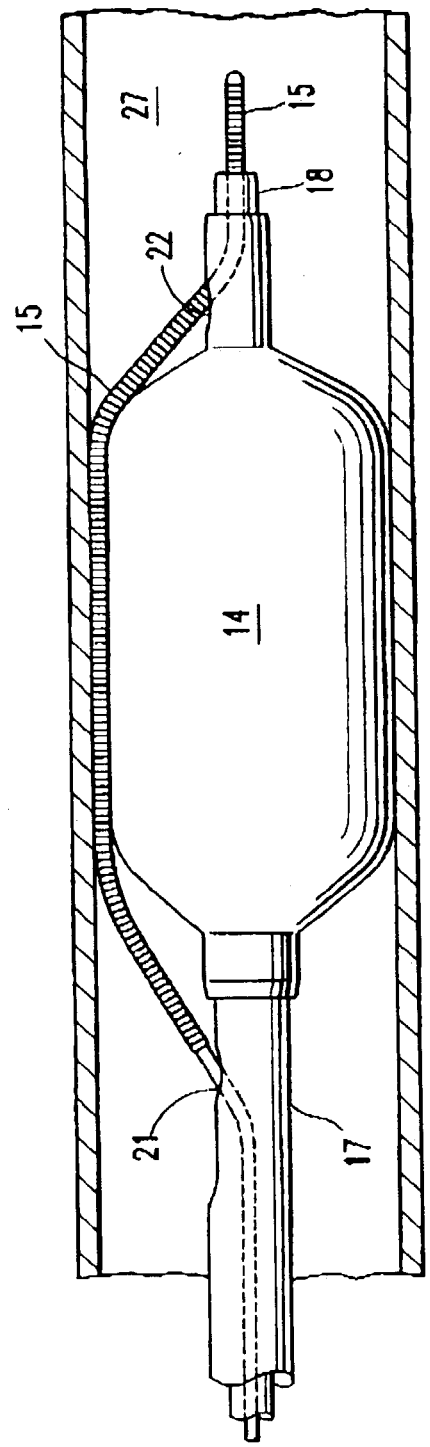
FIG. 5 illustrates the balloon catheter of FIG. 1, with the balloon fully inflated in a patient's body lumen.

FIG. 1 illustrates the balloon catheter 10 with the balloon across a stenotic region of the patient's blood vessel 27. The balloon is inflated by directing inflation fluid through the inflation lumen 12, to expand the balloon. FIG. 5 illustrates the balloon catheter of FIG. 1, with the balloon fully inflated, so that the balloon working length contacts and dilates the stenotic region. The section of the guidewire 15 extending along the outer surface of the balloon contacts the stenosed section of the blood vessel during inflation of the balloon 14. As a result, the section of the guidewire 15 frictionally engages the blood vessel wall, so that the balloon 14 has an insubstantial amount of longitudinal slippage proximally or distally from the desired position in the blood vessel 27. The balloon 14 is then deflated, and the balloon catheter 10 can be withdrawn proximally over the guidewire 15 leaving the guidewire in place, or withdrawn with the guidewire 15.

Figure 6:
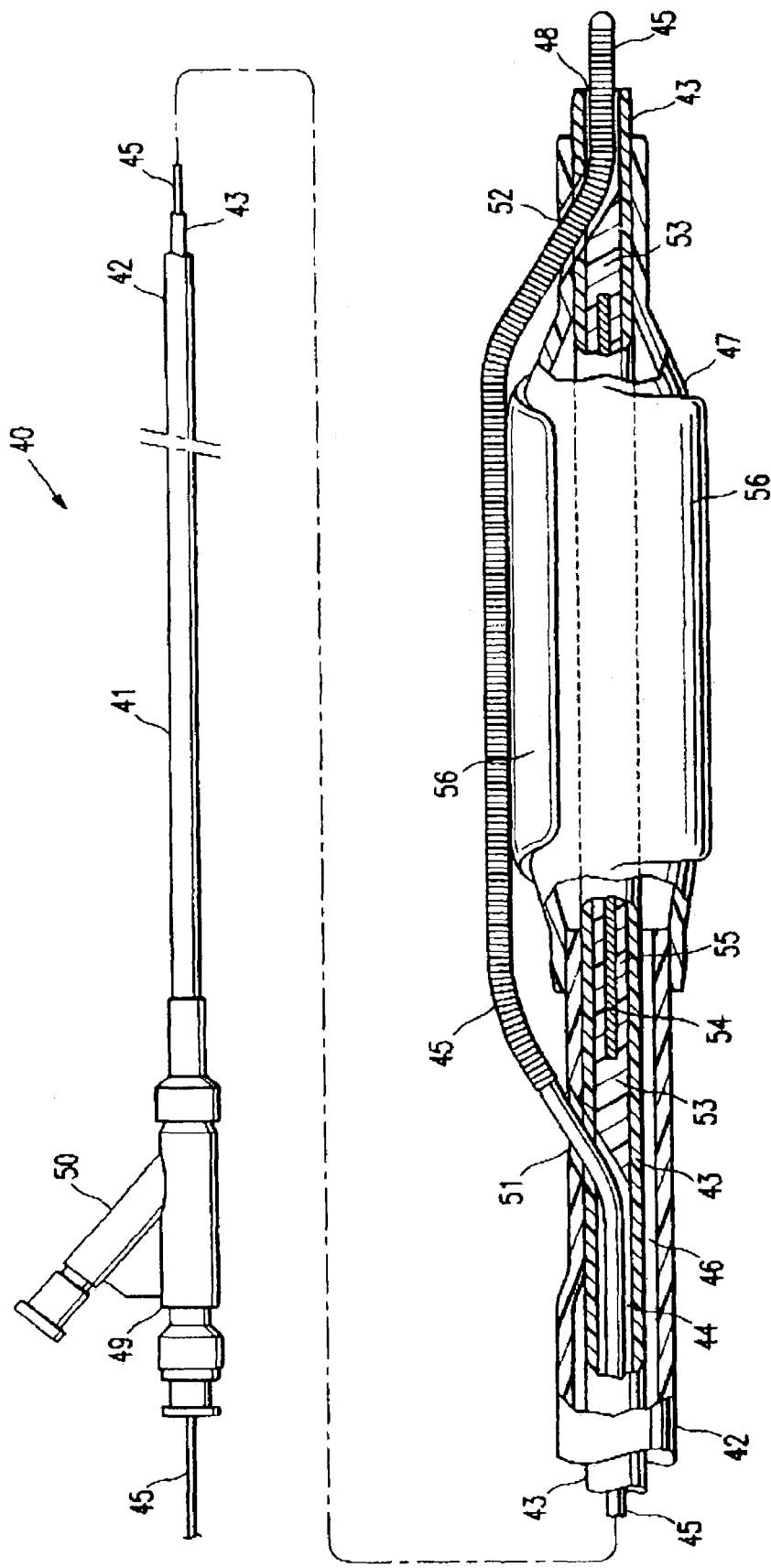
FIG. 6 is an elevational view, partially in section, of an alternative embodiment of an over-the-wire type balloon catheter which embodies features of the invention.

FIG. 6 illustrates an over-the-wire type balloon catheter 40 embodying features of the invention. Catheter 40 generally comprises an elongated catheter shaft 41 having an outer tubular member 42 and an inner tubular member 43. Inner tubular member 43 defines a guidewire lumen 44 configured to slidingly receive a guidewire 45, with a guidewire proximal port at the proximal end of the catheter, and a guidewire distal port 48 at the catheter distal end. The coaxial relationship between outer tubular member 42 and inner tubular member 43 defines annular inflation lumen 46. An inflatable balloon 47 disposed on a distal section of catheter shaft 41 has a proximal skirt section sealingly secured to the distal end of outer tubular member 42 and a distal skirt section sealingly secured to the distal end of inner tubular member 43, so that its interior is in fluid communication with inflation lumen 46. An adapter 49 at the proximal end of catheter shaft 41 is configured to provide access to guidewire lumen 44, and to direct inflation fluid through arm 50 into inflation lumen 46.

A proximal intermediate port 51 in communication with the guidewire lumen 44 is located proximal to the balloon 47 and distal to the guidewire proximal port, and a distal intermediate port 52 in communication with the guidewire lumen 44 is located distal to the balloon 47 and proximal to the guidewire distal port 48. The proximal and distal intermediate ports 51, 52 extend through a sidewall of the outer tubular member 42 and a sidewall of the inner tubular member 43. The discussion above relating to the intermediate ports 21, 22 of the embodiment of FIG. 1 applies to the intermediate ports 51, 52 of the over-the-wire catheter 40 of FIG. 6.

A support member 53 is in the guidewire lumen 44 between the proximal and distal intermediate ports 51, 52. Support member 53 comprises a metallic mandrel 54 surrounded by polymeric material 55. The polymeric material 55 forms the wedge-shaped ends of the support member 53, facilitating directing the guidewire through the intermediate ports 51, 52 as discussed above in relation to the embodiment of FIG. 1. The metallic mandrel 54 embedded in the polymeric material 55 may be formed using a variety of suitable methods. For example, in one embodiment, a metallic mandrel is placed in the lumen of a polymeric tube having a length longer than the metallic mandrel, and the assembly heated, causing the polymeric material 55 to flow and form the polymeric ends of the support member 53 at either end of the metallic mandrel 54.

In the embodiment of FIG. 6, the balloon is illustrated in a folded configuration, with folded wings 56 for introduction and advancement within the body lumen 27. In the figures illustrating the uninflated balloon, the distance between the inner surface of the balloon interior and the outer surface of the portion of the catheter shaft extending therethrough is exaggerated in the figures for ease of illustration. The guidewire 45 extends along an exposed outer surface of the folded balloon 47. In an alternative embodiment illustrated in FIG. 7 the guidewire extends underneath a folded wing 56 of the noninflated balloon 47. As best shown in FIG. 8, illustrating a transverse cross section of the distal section of the catheter of FIG. 7, taken along line 8-8, the balloon in the noninflated folded configuration prior to being inflated to an inflated configuration, has an outer surface with an exposed first section 57 and an unexposed second section 58 in the folded configuration. In the inflated configuration the balloon interior is filled with inflation fluid, so that the inflated configuration exposes both the first and second sections 57, 58 of the balloon outer surface, and the guidewire 45 becomes exposed (for contacting the wall of the body lumen as illustrated in FIG. 5). Thus in the embodiment of FIG. 7, the section of the guidewire 45 extending along the outer surface of the balloon extends at least in part along the outer surface unexposed section 58 of the balloon in the folded configuration.

The guidewire 15, 45 is a conventional guidewire, typically having a rounded outer surface and a coiled distal tip. In a presently preferred embodiment, the coiled distal tip of the guidewire typically has a length sufficiently long to extend along the length of the outer surface of the balloon 14, 47, with the coiled distal tip providing enhanced frictional contact with the wall of the patient's blood vessel 27 during inflation of the balloon 14, 47. Conventional guidewires for angioplasty and peripheral or neural dilatation procedures typically have an outer diameter of about 0.3 to about 0.45 mm, and a length of about 190 to about 300 cm, with a coiled distal tip having a length of about 2 to about 25 cm.

Although in the illustrated embodiments, the catheter shafts 11, 41 comprise inner and outer tubular members defining the inflation lumen therebetween, in an alternative embodiment, the shaft may comprise a dual-lumen extruded polymeric tubular member. FIG. 9 illustrates a transverse cross section of a dual-lumen extruded polymeric catheter shaft 70, having an inflation lumen 71 and a guidewire lumen 72. Although not illustrated, a support member such as a mandrel is typically provided in the distal end of the guidewire lumen 72, to extend distally beyond the distal end of the dual lumen shaft and through the interior of the balloon, similar to support member 29, 53 discussed above. Typically a tubular section of the catheter shaft does not extend beyond the distal end of the dual lumen shaft 70, so the support member in the balloon interior is not surrounded by the catheter shaft.

To the extent not previously discussed herein, the various catheter components may be formed and joined by conventional materials and methods. Outer tubular member can be formed by conventional techniques, such as by extruding and necking materials found useful in intravascular catheters such a polyethylene, polyvinyl chloride, polyesters, polyamide, polyimides, polyurethanes, and composite materials. Although illustrated as one-piece tubular members, it should be understood that the outer and inner tubular members 17, 18 may be formed of multiple tubular members or multi-layered tubular members. For example, the outer tubular member 17 typically comprises multiple tubular members joined end to end, to provide increasing flexibility distally along the length of the catheter.

The length of the balloon catheter 10, 40 is generally about 137 to about 145 centimeters, and typically about 140 centimeters for PTCA. The outer tubular member 14 distal section has an outer diameter (OD) of about 0.028 to about 0.036 inch (0.70-0.91 mm), and an inner diameter (ID) of about 0.024 to about 0.035 inch (0.60-0.89 mm), and the outer tubular member 14 proximal section has an OD of about 0.017 to about 0.034 inch (0.43-0.87 mm), and an inner diameter (ID) of about 0.012 to about 0.022 inch (0.30-0.56 mm). The inner tubular member 16 has an OD of about 0.017 to about 0.026 inch (0.43-0.66 mm), and an ID of about 0.015 to about 0.018 inch (0.38-0.46 mm) depending on the diameter of the guidewire to be used with the catheter. The balloon 14, 47 is typically about 8 to about 38 mm in length, with an inflated working diameter of about 1.5 to about 5 mm.

While the present invention has been described herein in terms of certain preferred embodiments, those skilled in the art will recognize that modifications and improvements may be made without departing from the scope of the invention. For example, although illustrated with support member 29, 53 in a lumen of the shaft, in alternative embodiments, at least a section of the support member is not in a lumen of the shaft, so that the support member extends through the balloon interior without a portion of the tubular shaft therearound. Moreover, while individual features of one embodiment of the invention may be discussed or shown in the drawings of the one embodiment and not in other embodiments, it should be apparent that individual features of one embodiment may be combined with one or more features of another embodiment or features from a plurality of embodiments.

What is claimed is:

1. A balloon catheter, comprising:
   a) an elongated tubular shaft having a proximal end, a distal end, an inflation lumen, a guidewire lumen, a guidewire proximal port, and a guidewire distal port at the distal end of the shaft;
   b) a balloon on a distal shaft section, having a proximal end, a distal end, and an inflatable section having a proximal end, a distal end, and an interior in fluid communication with the inflation lumen, with a portion of the tubular shaft extended through the balloon interior and bonded to a distal skirt of the balloon; and
   c) a proximal intermediate port in communication with the guidewire lumen and located proximal to the inflatable section of the balloon and distal to the guidewire proximal port, and a distal intermediate port in communication with the guidewire lumen and located distal to the distal end of the inflatable section of the balloon and proximal to the guidewire distal port, the intermediate ports being configured to slidably receive a guidewire therethrough so that the guidewire extends into or out of a proximal section of the guidewire lumen through the proximal intermediate port and extends into or out of a distal section of the guidewire lumen through the distal intermediate port, and the proximal section of the guidewire lumen located proximal to the proximal intermediate port is not in communication with the portion of the tubular shaft extending through the interior of the balloon.

2. The balloon catheter of claim 1 wherein the distal portion of the guidewire lumen located distal to the distal intermediate port is not in communication with the portion of the tubular shaft extending in the interior of the balloon.

3. The balloon catheter of claim 1 wherein the guidewire lumen at the intermediate ports is oriented to open outwardly in a direction pointing toward the balloon.

4. The balloon catheter of claim 1 wherein the guidewire proximal port is distal to the proximal end of the shaft.

5. The balloon catheter of claim 1 having a support member in at least a part of the guidewire lumen located between the proximal and distal intermediate ports.

6. The balloon catheter of claim 1 wherein the shaft comprises an outer tubular member defining at least a section of the inflation lumen, and an inner tubular member defining at least a section of the guidewire lumen and disposed at least in part in the inflation lumen, and the balloon has a proximal end secured to the outer tubular member and a distal end secured to the inner tubular member so that the portion of the tubular shaft extending in the balloon interior is formed by a distal portion of the inner tubular member.

7. The balloon catheter of claim 6 wherein the inner tubular member has a support member with a proximal end located at the proximal intermediate port and a distal end located at the distal intermediate port, so that the support member extends between the proximal and distal intermediate ports.

8. A balloon catheter, comprising:
a) an elongated shaft comprising an outer tubular member defining an inflation lumen, and an inner tubular member disposed at least in part in the inflation lumen and defining at least a section of the guidewire lumen, the inner tubular member having a proximal guidewire port, and a distal guidewire port at a distal end of the shaft;
b) an inflatable balloon on a distal shaft section having inflatable section with an interior in fluid communication with the inflation lumen, and having a distal portion of the inner tubular member extending in the balloon interior;
c) a proximal intermediate port proximal to the inflatable section of the balloon and distal to the guidewire proximal port, and a distal intermediate port distal to the inflatable section of the balloon and proximal to the guidewire distal port, the intermediate ports being in communication with the guidewire lumen and being configured to slidably receive a guidewire therethrough; and
d) a support member in the guidewire lumen between the proximal and distal intermediate ports, which at least partially occludes the guidewire lumen, and which has a wedge-shaped proximal end surface at least a portion thereof being located at the proximal intermediate port.

9. The balloon catheter of claim 8 wherein the support member fully occludes the guidewire lumen, so that a section of the guidewire lumen located proximal to the proximal intermediate port is not in fluid communication with the section of the guidewire lumen extending in the interior of the balloon.

10. The balloon catheter of claim 8 wherein the support member comprises a mandrel.

11. The balloon catheter of claim 8 wherein the support member has a wedge-shaped distal end surface at least a portion thereof being located at the distal intermediate port.

12. The balloon catheter of claim 8 wherein the inner tubular member has a first section coaxially disposed in the outer tubular member lumen, and a second section longitudinally adjacent to the first section and bonded to the outer tubular member at the proximal intermediate port.

13. A balloon catheter, comprising:
a) an elongated tubular shaft having a proximal end, a distal end, an inflation lumen, a guidewire lumen, a guidewire proximal port, and a guidewire distal port at the distal end of the shaft;
b) a balloon on a distal shaft section, having a proximal end, a distal end, and an inflatable section having an interior in fluid communication with the inflation lumen;
c) a proximal intermediate port in communication with the guidewire lumen and located proximal to the inflatable section of the balloon and distal to the guidewire proximal port, and a distal intermediate port in communication with the guidewire lumen and located distal to the inflatable section of the balloon and proximal to the guidewire distal port, the intermediate ports being configured to slidably receive a guidewire therethrough; and
d) a support member between the proximal and distal intermediate ports and extending through the interior of the balloon and having a proximal end which is not proximal to the proximal intermediate port, and a distal end which is not distal to the distal intermediate port.

14. A balloon catheter system, comprising:
a) a balloon catheter, comprising:
   i) an elongated shaft having a proximal end, a distal end, an inflation lumen, a guidewire lumen, a guidewire proximal port, and a guidewire distal port at the distal end of the shaft;
   ii) a balloon on a distal shaft section, having a proximal end, a distal end, and an inflatable section having a proximal end, a distal end, and an interior in fluid communication with the inflation lumen, with a portion of the tubular shaft extending in the balloon interior; and
   iii) a proximal intermediate port proximal to the inflatable section of the balloon and distal to the guidewire proximal port, and a distal intermediate port distal to the distal end of the inflatable section of the balloon and proximal to the guidewire distal port, the intermediate ports being in communication with the guidewire lumen and being configured to slidably receive the guidewire therethrough; and
b) a guidewire in the guidewire lumen proximal and distal to the balloon, and extending through the proximal and distal intermediate ports so that a section of the guidewire extends along an outer surface of the balloon.

15. The balloon catheter system of claim 14 wherein the balloon outer surface has an exposed section in a noninflated configuration prior to being inflated to an inflated configuration, and the section of the guidewire extending along the outer surface of the balloon extends along the outer surface exposed section of the balloon in the noninflated configuration.

16. The catheter system of claim 14 wherein the guidewire has a coiled distal tip having a length sufficiently long so that a proximal end of the coiled distal tip is proximal to the distal end of the balloon and a distal end of the coiled distal tip is distal to the distal end of the catheter, so that at least a section of the coiled distal tip extends along the outer surface of the balloon and through the guidewire distal port.

17. The catheter system of claim 14 having a support member in at least a portion of the guidewire lumen located between the proximal and distal intermediate ports.

* * * * *